US005627068A

United States Patent [19]
Kujumdzieva et al.

[11] Patent Number: 5,627,068
[45] Date of Patent: May 6, 1997

[54] *MONASCUS PURPUREUS* STRAIN PRODUCER OF PIGMENTS AND BY-PRODUCTS

[76] Inventors: Anna V. Kujumdzieva, c/s West Park, bl. 124, en B, ap 2, Sofia, 1373, Bulgaria; Jean N. Hallet, 13 rue de la Gourmette, Nantes, 44300, France; Valentin A. Savov, c/s West Park, bl. 124, en B, ap 2, Sofia, 1373, Bulgaria; Tanya V. Rasheva, c/s Darvenitsa, bl. 13, A, ap 24, Sofia, 1756, Bulgaria

[21] Appl. No.: 493,691

[22] Filed: Jun. 22, 1995

[30] Foreign Application Priority Data

Jun. 24, 1994 [BG] Bulgaria ................................. 98875

[51] Int. Cl.$^6$ ...................................................... C12N 1/20
[52] U.S. Cl. ...................... 435/254.1; 435/119; 435/125; 435/171; 435/911
[58] Field of Search ................................ 435/254.1, 911, 435/125, 119, 171

[56] References Cited

U.S. PATENT DOCUMENTS

| | | | |
|---|---|---|---|
| 4,145,254 | 3/1979 | Shepherd et al. | 435/911 |
| 4,323,648 | 4/1982 | Tanzawa et al. | 435/911 |
| 4,418,080 | 11/1983 | Yueh et al. | 435/254.1 |
| 4,418,081 | 11/1983 | Rashbaum et al. | 435/254.1 |

*Primary Examiner*—Herbert J. Lilling
*Attorney, Agent, or Firm*—Kenneth A. Roddy

[57] ABSTRACT

A *Monascus purpureus* 94-25 (NBIMCC 2325) strain microorganism produces pigments and biologically active products when cultivated on a culture medium based on waste disposals from the milk industry. The pigmented product obtained possesses superoxide dismutase and antioxidant properties and has applications in the food and beverage industry and cosmetics industry. The present process is suitable for large scale manufacture and, by its application, a large amount of waste and by-products from the milk processing industry is utilized and thus an ecologically clean and wasteless technology is created.

3 Claims, No Drawings

MONASCUS PURPUREUS STRAIN PRODUCER OF PIGMENTS AND BY-PRODUCTS

BACKGROUND OF THE INVENTION

1. Field of the Invention

This invention relates generally to fungi of the genus Monascus and processes for the production of Monascus pigment, and more particularly to a newly isolated *Monascus purpureus* 94-25 (NBIMCC 2325) strain which utilizes lactose to produce pigments and biologically active products, and processes for producing pigments and biologically active products utilizing the *Monascus purpureus* 94-25 (NBIMCC 2325) strain.

2. Brief Description of the Prior Art

Fungi, belonging to the genus Monascus are well known since centuries in the countries of South East Asia. They are used in the fermentative production of red rice, red soyabean cheese and curd and red rice wine. Fungi from the genus Monascus synthesize red, yellow, and orange pigments characterized by thermostability and high colouring abilities which currently determines their wide application in food and beverage industry and cosmetics.

Different strains, such as *Monascus purpureus, Monascus anka, Monascus major,* and *Monascus rubiginosus* are known to be used for pigment production, as disclosed in St. Martin, U.S. Pat. No. 4,927,760 and Shepherd et al, U.S. Pat. No. 4,145,254.

These microorganisms are cultivated on different solid and liquid synthetic and complex substrates. The most widely used culture media are those based on grains, such as rice, barley, and wheat, and usually the cultivation process requires 14–18 days. Rashbaum et al, U.S. Pat. No. 4,418,081 discloses the production of pigments produced by the growth of the mold of the genus Monascus on an oat substrate. Yueh et al, U.S. Pat. No. 4,418,080 discloses the production of pigments produced by the growth of the mold of the genus Monascus on both wheat and barley substrates.

Under these conditions predominantly water insoluble pigments are produced and in most cases a post fermentation chemical modification is needed, as disclosed in U.S. Pat. No. 3,993,789 to Moll et al.

Problems of the above type are solved partly through another known production procedure comprising cultivating fungi of the Monascus genus on a culture media based on milk or whey permeate, as taught by Bulgarian Patent 60416. However, the fungi used in that process does not have the ability to assimilate lactose.

The present invention is distinguished over the prior art in general, and these patents in particular by the use of a *Monascus purpureus* 94-25 (NBIMCC 2325) strain microorganism which assimilates lactose and synthesizes complex substances (pigments, methylketones, lipids and inhibitors) when cultivated on substrates of by-products from milk processing. Red and orange pigments and biologically active products are produced by cultivating the *Monascus purpureus* 94-25 (NBIMCC 2325) strain on a culture medium containing milk or whey permeate, which may include lactose assimilation inducers. The strain is cultivated for from 2 to 4 days at a temperature of from 28° C. to 37° C. on a nutrient medium comprising milk or whey permeate at a pH of from 4 to 7 and aerated from 0.3 to 1 l/l minutes. The pigments obtained are characterized by high superoxide dismutase and antioxidant activity and are suitable as a replacement for the superoxide dismutase enzyme now used in the food and beverage industry, cosmetics, and medicine.

The *Monascus purpureus* 94-25 (NBIMCC 2325) strain of the present invention differs from other strains belonging to genus Monascus by its capability for lactose assimilation. The comparative characteristics of the newly isolated strain *Monascus purpureus* 94-25 (NBIMCC 2325) and different strains, belonging to the genus Monascus are described below.

SUMMARY OF THE INVENTION

It is therefore an object of the present invention to provide a strain of microorganism belonging to the genus Monascus which utilizes lactose, synthesizes different biologically active substances and is suitable for large scale industrial manufacture.

It is another object of this invention to provide a strain of microorganism belonging to the genus Monascus which assimilates lactose and produces pigments.

Another object of this invention is to provide a method for producing pigmented antioxidant products containing superoxide dismutase by cultivating a *Monascus purpureus* 94-25 (NBIMCC 2325) strain on a nutrient medium comprising milk or whey permeate.

Another object of this invention is to provide a method for producing bioactive products especially lipids, methylketones and monacolins by cultivating a *Monascus purpureus* 94-25 (NBIMCC 2325) strain on a nutrient medium comprising milk or whey permeate.

A further object of this invention is to provide a method for producing pigments and biologically active products by cultivating a *Monascus purpureus* 94-25 (NBIMCC 2325) strain on a nutrient medium comprising milk or whey permeate which are suitable for use in the food and beverage industry and cosmetics industry.

A still further object of this invention is to provide a method for producing pigments and biologically active products by cultivating a *Monascus purpureus* 94-25 (NBIMCC 2325) strain on a nutrient medium which will utilize a large amount of waste and by-products from the milk processing industry.

Other objects of the invention will become apparent from time to time throughout the specification and claims as hereinafter related.

The above noted objects and other objects of the invention are accomplished by the use of a *Monascus purpureus* 94-25 (NBIMCC 2325) strain microorganism which assimilates lactose and synthesizes complex substances (pigments, methylketones, lipids and inhibitors) when cultivated on substrates of by-products from milk processing. Red and orange pigments and biologically active products are produced by cultivating the *Monascus purpureus* 94-25 (NBIMCC 2325) strain on a culture medium containing milk or whey permeate, which may include lactose assimilation inducers. The strain is cultivated for from 2 to 4 days at a temperature of from 28° C. to 37° C. on a nutrient medium comprising milk or whey permeate at a pH of from 4 to 7 and aerated from 0.3 to 1.0 liter/liter/minute. The pigments obtained are characterized by high superoxide dismutase and antioxidant activity and are suitable as a replacement for the superoxide dismutase enzyme now used in the food and beverage industry, cosmetics, and medicine.

DESCRIPTION OF THE PREFERRED EMBODIMENT

The newly isolated strain *Monascus purpureus* 94-25 (NBIMCC 2325) was deposited on Jun. 6, 1993 with the National Bank of Industrial Microorganisms and Cell Cultures (NBIMCC), 1113 Sofia, 125 Tsarigradsko chausse blvd., block 2, Bulgaria, and was issued Accession No. 2325 on Jun. 15, 1993, and is readily available from NBIMCC as indicated by the Accession No. given in parentheses. The newly isolated strain Monascus purpureus 94-25 (NBIMCC 2325) has the following characteristics:

The Monascus purpureus 94-25 (NBIMCC 2325) strain is isolated from red rice and is characterized according to the taxonomic criteria of Hawksworth and Pitt A New Taxonomy Of Monascus sp., based on cultural and microscopical characters, Austr. J. Bot., 31 (1), 51–61, 1951.

Growth on Chapec-Yeast Extract Agar at 25° C. for 7 days. Monascus purpureus 94-25 (NBIMCC 2325) forms colonia 13–16 mm diameter, with rough surface and rare aerial growth, with white or red mycellium. Small drops of red exudates can be observed on the surface. Soluble orange or red pigment is released in the agar around the colony. Cleistothrcia and aleiroconidia formation can be observed. On the same medium, cultivated at 37° C. for 7 days the Monascus purpureus 94-25 (NBIMCC 2325) strain forms colonies 22–27 mm large, similar to the above described, but weakly pigmented. The strain also forms cleistothecia and aleiroconidia.

Growth on Malt Extract Agar at 25° C. for 7 days. Monascus purpureus 94-25 (NBIMCC 2325) forms colonies with 18–24 mm diameter. At the beginning of cultivation the mycellium is white and later it is pigmented in orange. Aleiroconidia are observed.

Growth on 25% Glycerol-Nitrate Agar at 25° C. for 7 days. Monascus purpureus 94-25 (NBIMCC 2325) forms 5–10 mm, folded colonies, similar to those observed on Chapec - Yeast Extract Agar but white in colour.

Morphological Characteristics: Monascus purpureus 94-25 (NBIMCC 2325) forms abundant mycellium, with irregular, branced, hyphae, 2–4 μm wide, the walls are often with a lot of crystal orange or red structures. The aleiroconidia are formed in a single way or on short chains, terminally on the hyphae. The conidia are with thick smooth walls, up to 3–4 on a chain with size 8–10 μm. The cleistothecia are globoid, formed on single hyphae with diameter from 30–50 μm. The peridium is hialine, consists of hiphae, forming a sac. The asci are full with spores. The ascospores are 4–5 μm large, hyaline, smooth, oval 4–8 by number.

Sexual reproduction: Sexual reproduction of the Monascus purpureus 94-25 (NBIMCC 2325) strain is observed on a culture medium consisting of (g/l): glucose= 40, $KH_2PO_4$=1, $MgSO_47H_2O$=0.5, NaCl=0.5, $NH_4Cl$=0.5, $FeSO_47H_2O$=0.01, $ZnSO_47H_2O$=0.001, agar=20, and a pH of 6.0. Asexual reproduction is observed on the same medium but with 3 g/l $NaNO_3$ as a nitrogen source. The cultivation is carried out in petri dishes, at 30° C. for 3–7 days.

Tolerance to NaCl: The Monascus purpureus 94-25 (NBIMCC 2325) strain is tolerant to 6% NaCL.

Growth Temperature: minimal 14° C.
optimal 34° C.
maximal 46° C.

The Monascus purpureus 94-25 (NBIMCC 2325) strain is prototroph.

Biochemical characteristics: The Monascus purpureus 94-25 (NBIMCC 2325) strain differs from other strains belonging to genus Monascus by its capability for lactose assimilation. The comparative characteristic for different carbon source utilization of the newly isolated strain Monascus purpureus 94-25 (NBIMCC 2325) and different strains, belonging to genus Monascus, from different strain collections is shown in Table 1 below. The assimilation test is performed in a submerged shaken culture, on Chapec-Dox culture medium, containing (g/l): $KH_2PO_4$=1, $MgSO_47H_2O$=0.5, NaCl=0.5, $NaNO_3$=3, $FeSO_47H_2O$=0.01, $ZnSO_47H_2O$=0.001, a pH of 6.0, and concentration of the carbon source at 20 g/l. The cultivation process is carried out in 500 ml Erlenayer flasks, on 100 ml medium, on Shutel apparatus, at 30° C. for 7 days. The growth is determined gravimetrically.

TABLE 1

| Carbon source | Microorganisms used | | | |
| --- | --- | --- | --- | --- |
| | Monascus purpureus 94-25 | Monascus purpureus CBS 109.07 | Monascus anka IFO 4478 | Monascus ruber DSM 62748 |
| glucose | + | + | + | + |
| lactose | + | − | − | − |
| fructose | + | + | + | + |
| galactose | + | + | − | − |
| melibiose | + | + | − | + |
| maltose | + | + | + | + |
| raffinose | + | + | + | + |
| sucrose | + | + | + | − |
| xylose | + | + | + | + |
| xylitol | − | + | + | + |
| ribitol | + | + | + | + |
| sorbitol | + | + | + | − |
| erythritol | + | − | − | + |
| m-inositol | − | − | − | + |
| galactitol | + | + | + | + |
| manitol | + | + | + | + |
| glycerol | + | + | + | − |
| ethanol | + | + | + | − |
| methanol | − | − | − | − |

The galactopiranosides investigated (galactose, melibiose, isopropyl-β-D-thiogalactoside) and glycerol show a sinergistic effect on the lactose assimilation, when added in concentrations of from 0.01% to 1%. Similar effect on the lactose utilization possess different aminoacids (glutamic acid, aspargin acid, threonine, and tryptophan in concentrations of from 0.01% to 0.1%), as well as dry permeate in quantities of from 0.1% to 2% (Table 2).

TABLE 2

| Chapec-Dox culture medium containing 2% lactose as carbon source | % lactose assimilation of Monascus purpureus 94-25 strain |
| --- | --- |
| without supplements | 35 |
| mixture of amino acids 0.1% | 48 |
| dry permeate 1% | 75 |
| casein hydrolizate 1% | 70 |

Fermentation of carbon sources: The Monascus purpureus 94-25 (NBIMCC 2325) strain does not ferment lactose, maltose, galactose, raffinose, sucrose and glucose.

The advantages of the new strain can be summarized as follows:

The strain Monascus purpureus 94-25 (NBIMCC 2325) is capable of synthesizing pigments in amounts suitable for large scale production.

The strain *Monascus purpureus* 94-25 (NBIMCC 2325) possesses the ability to assimilate lactose and to synthesize complex substances (pigments, methylketones, lipids and inhibitors) when it is cultivated on substrates of by-products from milk processing.

The pigments obtained are characterized by high superoxide dismutase and antioxidant activity (Table 3) and can find application as a replacement for the superoxide dismutase enzyme now used in the food and beverage industry, cosmetics, and medicine.

TABLE 3

| Chromatographycally pure pigments | Superoxide dismutase activity U/mg pigment | Antioxidant activity OU/mg pigment |
|---|---|---|
| red | 3.2 +/− 0.15 | 100 +/− 4 |
| orange | 4.02 +/− 0.10 | 130 +/− 3 |
| yellow | 4.36 +/− 0.09 | 180 +/− 2 |

Using the strain *Monascus purpureus* 94-25 (NBIMCC 2325) in a large scale manufacture, a great volume of waste from the milk industry can be utilized and a wasteless and ecologically clean technology is created.

EXAMPLE 1

Cultivation of the *Monascus Purpureus* 94-25 (NBIMCC 2325) strain. The strain is maintained on solid media containing (g/l): glucose=20, peptone=10, malt extract=5, agar=20, at a pH of 6. The cultivation is carried out at 30° C. for 7 days. The main fermentation is performed on a 10 l Bioengineering fermentor at 30° C., a pH of 6, $pO_2$ of 30%, agitation at 300 r.p.m., and aeration 0.3 l/l/min. The culture medium contains (g/l): glucose =20, sodium glutamate=5, yeast extract=1, $MgSO_4 7H_2O$=0.5, $KH_2PO_4$=1, NaCl=0.5, at a pH of 6. A 48 hour shaken culture on a liquid maintainance medium is used as an inoculum. The maxium pigment amount is observed on the 72nd hour of cultivation. The obtained product is separated from the biomass by centrifugation. The residual concentrations of sugar, nitrogen, phosphorus, the pigment amount, and the dry weight are determined. The quantity of the obtained pigment is 550–600 OU/mg dry product.

EXAMPLE 2

Production of a red pigment by *Monascus purpureus* 94-25 (NBIMCC 2325) strain using milk or whey permeates. The cultivation is performed under the conditions described in EXAMPLE 1 above. The culture medium is permeate from milk or whey, obtained after ultrafiltration on DDS equipment on 5 kD membranes, characterized by (g/l): lactose=45–50, protein=0.9–1, aminoacids=0.5, nitrogen=1.0–1.3, and phosphorus=2.0–2.5. Additionally galactose, melibiose, glycerin in concentrations of 0.6% and isopropyl-β-D-thiogalactoside in a concentration of 0.1% are added to the permeate (Table 4). The cultivation is carried out for 72 hours and the product obtained is separated from the biomass by centrifugation. The filtrate is freeze dried. The obtained product has the following characteristics: powderlike, red, watersoluble product, containing (mg/g dry product): pigment=600–800 Optical Units, protein=16.8, proteolitic activity=1.5 U/mg protein.

TABLE 4

| Carbon source | Lactose consumption % | Pigment production OU/mg dry product | Ratio 500/400 nm |
|---|---|---|---|
| lactose 4% | 30 | 580–640 | 1.46 |
| lactose 4% glycerol 0.6% | 50 | 650–700 | 1.50 |
| lactose 4% galactose 0.6% | 58 | 720–780 | 1.58 |
| lactose 4% melibiose 0.6% | 60 | 800–820 | 1.65 |
| lactose 4% isopropyl-β-D-thiogalactoside 0.1% | 70 | 800–850 | 1.72 |

EXAMPLE 3

Production of an orange pigment using *Monascus purpureus* 94-25 (NBIMCC 2325) strain. The cultivation conditions are the same as described in EXAMPLE 1 above. The culture medium for the main fermentations contains (g/l): $MgSO_4 7H_2O$=0.5, NaCl=0.5, $KH_2PO_4$=1.0, $(NH_4)_2SO_4$=0.5, at a pH of 6-0. As a carbon source glucose in a concentration of 20 g/l is used. The fermentation process lasts 72 hours, and as a result large orange amorphous crystals are obtained. The cultural liquid is separated by filtration and the obtained product, rewashed and freeze dried, has the following characteristics: powderlike substance coloured in orange containing 650–700 Optical Units per mg dry substance.

EXAMPLE 4

Production of an orange pigment using *Monascus purpureus* 94-25 (NBIMCC 2325) strain and milk or whey permeate. The cultivation conditions are the same as described in EXAMPLE 1 above. The culture medium for the main fermentations consists of (g/l): milk or whey permeate 1:1, NH4CL=0.5, at a pH of 6.0. Additionally galactose, melibiose, glycerol and isopropyl-β-D-thiogalactoside in a concentration of 0.6% are added. At the end of the fermentation great orange amorphous crystals are obtained which are separated from the cultural broth by filtration and after rewashing they are freeze dried. The results of the different variants are shown in Table 5.

TABLE 5

| Carbon source | Lactose consumption % | Pigment production OU/mg dry product | Ratio 500/400 nm |
|---|---|---|---|
| lactose 2% | 35 | 540–580 | 0.710 |
| lactose 2% glycerol 0.6% | 55 | 620–650 | 0.587 |
| lactose 2% galactose 0.6% | 64 | 700–750 | 0.420 |
| lactose 2% melibiose 0.6% | 60 | 700–730 | 0.456 |
| lactose 2% isopropyl-β-D-thiogalactoside 0.1% | 65 | 400–480 | 0.415 |

EXAMPLE 5

Production of methylketones using *Monascus purpureus* 94-25 (NBIMCC 2325) white variant strain. The inoculum for the fermentation process is prepared on a submerged culture medium containing (g/l): lactose=20, galactose=8, $KH_2PO_4$=1, $MgSO_4 7H_2O$=0.5, NaCl=0.5, $NaNO_3$=3, $FeSO_4 7H_2O$=0.01, $ZnSO_4 7H_2O$=0.001, and a pH of 6.0. The cultivation is carried out in 500 ml flasks containing 100 ml broth on a Shutel apparatus at 30° C. for 24 hours. The methylketone biosynthesis is performed on a culture medium comprising milk or whey permeate, dilluted 1:1 containing 0.7% fatty acids ($C_6$–$C_{10}$). As a second variant to increase fatty acid content 0.5 mmol mixture of C6 C8, C10 are added. The cultivation is carried out in a 10 l Bioengineering fermentor at 30° C., pH 6, $pO_2$ 30%, agitation at 300 r.p.m, aeration=0.8 l/l/min, for 48 hours. After the 24th hour of the fermentation process the fatty acids and methylketones contained through gas chromatography, and growth by dry weight are determined. The results for the obtained methylketones after the fatty acids transformation by the fungus are shown in Table 6.

TABLE 6

| Culture medium | Methylketones % | Residual concentration of fatty acids % | Dry weight g/l |
|---|---|---|---|
| permeate 1:1 | 0.45 | 0.15 | 2.45 |
| permeate 1:1+ 0.5 mM mixture of fatty acids ($C_6$–$C_{10}$) | 0.66 | 0.08 | 3.63 |

EXAMPLE 6

Lipid biosynthesis using *Monascus purpureus* 94-25 (NBIMCC 2325) strain red and white variants. The cultivation conditions are the same as in EXAMPLE 1 above, except that the air supply is 1 l/l/min. The culture medium of Chapec-Dox, consisting of (g/l): glucose=40, $KH_2PO_4$=1, $MgSO_4 7H_2O$=0.5, NaCl=0.5, $NH_4Cl$=0.5, $FeSO_4 7H_2O$=0.01, $ZnSO_4 7H_2O$=0.001, at a pH of 6.0, is used, except in this culture medium, whey or milk permeate containing (g/l): lactose=40–45, organic nitrogen=1.0, phosphorus=2.0, amino acids=0.5, and protein=0.9, is used. Additionally 8 g/l galactose are added. The lipid biosynthesis is controlled during the fermentation process. The results of the qualitative and quantitative lipid content are shown in Table 7.

TABLE 7

| Time of cultivation h | Dry weight g/l | Total lipid amount % | Lipids % | | |
|---|---|---|---|---|---|
| | | | neutral lipids | phospho lipids | glyco- lipids |
| 24 | 1.62 | 13.12 | 81.34 | 10.22 | 8.44 |
| 48 | 2.54 | 44.22 | 81.35 | 9.02 | 9.02 |
| 72 | 3.48 | 63.12 | 81.45 | 10.44 | 8.11 |

The total lipid amount is determined gravimetrically. The different lipid classes are determined by Thin Layer Chromatography on Kieselgel 60 $F_{254}$ plates and as mobile phases n-hexane:diethyl ether:acetic acid=65:15:1; chlorophorm:ethanol:water=80:20:2; and chlorophorm:methanol:water=65:15:4 are used. The quantitative determination is performed on a Dessaga CD60 densitometer, after spot visualization with uranilacetate.

EXAMPLE 7

Production of monacolins. *Monascus purpureus* 94-25 (NBIMCC 2325) strain white variant is cultivated at 28° C. for 7 days under the following conditions: culture medium comprising milk or whey permeate 100%, glycerol=20, galactose=8, at a pH of 6.5. The cultivation is performed on a 10 l Bioengineering fermentor, agitation at 300 r.p.m., air supply of 0.6 l/l/min, and $pO_2$ 30%. At these conditions, *Monascus purpureus* 94-2S produces dehydromonacolin L, monacolin X and monacolin K. Samples are taken every 12 hours and 2 ml culture broth are two times extracted with 10 ml ethylacetate at pH 3. The organic solvent layer is evaporated to dryness and additionally dryed above $Na_2SO_4$. The dryed residue is dissolved in 2 ml methanol and the monacolin content is determined by HPLC, on a Silica ODS column using 0.1% $H_3PO_4$:acetonitrile=55:45 as eluent. Under these conditions pure fractions of monacolin X, L, K, inhibitors of cholesterol biosynthesis are obtained.

While this invention has been described fully and completely with special emphasis upon preferred embodiments, it should be understood that within the scope of the appended claims the invention may be practiced otherwise than as specifically described herein.

We claim:

1. A biologically pure strain of *Monascus purpureus* 94-25 (NBIMCC 2325) which assimilates lactose and produces pigments and biologically active products.

2. The biologically pure strain of *Monascus purpureus* 94-25 (NBIMCC 2325) according to claim 1 wherein said strain is cultivated for from 2 to 4 days at a temperature of from 28° C. to 37° C. on a nutrient medium comprising milk or whey permeate at a pH of from 4 to 7 and aerated from 0.3 to 1.0 liter/liter/minute.

3. The biologically pure strain of *Monascus purpureus* 94-25 (NBIMCC 2325) according to claim 1 wherein said strain is cultivated for from 2 to 4 days at a temperature of from 28° C. to 37° C. on a nutrient medium comprising milk or whey permeate and lactose assimilation inducers at a pH of from 4 to 7 and aerated from 0.3 to 1.0 liter/liter/minute.

* * * * *